United States Patent
Hack

(10) Patent No.: US 7,210,847 B2
(45) Date of Patent: May 1, 2007

(54) INTRAORAL X-RAY SENSOR

(75) Inventor: Alexander Hack, Biberach (DE)

(73) Assignee: Kaltenbach & Voigt GmbH (DE)

( * ) Notice: Subject to any disclaimer, the term of this patent is extended or adjusted under 35 U.S.C. 154(b) by 0 days.

(21) Appl. No.: 11/235,477

(22) Filed: Sep. 26, 2005

(65) Prior Publication Data

US 2006/0067462 A1 Mar. 30, 2006

Related U.S. Application Data

(63) Continuation of application No. PCT/EP2004/003126, filed on Mar. 24, 2004.

(30) Foreign Application Priority Data

Mar. 24, 2003 (DE) ................ 103 13 044
Oct. 6, 2003 (DE) ................ 103 46 287

(51) Int. Cl.
*H01J 31/49* (2006.01)
(52) U.S. Cl. ............... 378/189; 378/191; 206/455
(58) Field of Classification Search ............... 378/189, 378/191, 184; 250/370.09, 370.11, 208.1; 206/455

See application file for complete search history.

(56) References Cited

U.S. PATENT DOCUMENTS

| | | | |
|---|---|---|---|
| 4,912,740 A * | 3/1990 | Liese, Jr. ................ 378/169 |
| 5,270,491 A * | 12/1993 | Carnall et al. ............ 174/52.4 |
| 5,434,418 A | 7/1995 | Schick ................... 250/370.11 |
| 5,510,623 A | 4/1996 | Sayag et al. ........... 250/370.11 |
| 5,514,873 A | 5/1996 | Schulze-Ganzlin et al. . 250/394 |
| 5,633,461 A * | 5/1997 | Kakizaki et al. .............. 73/493 |
| 6,025,598 A * | 2/2000 | Tago ..................... 250/370.01 |
| 6,069,935 A | 5/2000 | Schick et al. .............. 378/98.8 |
| 6,125,529 A * | 10/2000 | Rosen et al. ................... 29/612 |
| 6,169,781 B1 | 1/2001 | Doebert et al. ........... 378/98.8 |
| 6,383,160 B1 * | 5/2002 | Madsen ....................... 604/10 |
| 6,404,854 B1 | 6/2002 | Carroll et al. ............. 378/98.8 |
| 6,613,692 B1 * | 9/2003 | Toshima et al. ............ 438/745 |
| 6,700,126 B2 * | 3/2004 | Watanabe ............. 250/370.09 |
| 2005/0056789 A1* | 3/2005 | Spahn et al. ........... 250/370.09 |

FOREIGN PATENT DOCUMENTS

| | | |
|---|---|---|
| DE | 4402114 A1 | 7/1995 |
| DE | 29717432 U1 | 3/1999 |

\* cited by examiner

*Primary Examiner*—Edward J. Glick
*Assistant Examiner*—Jurie Yun
(74) *Attorney, Agent, or Firm*—Mayback & Hoffman, P.A.; Gregory L. Mayback

(57) ABSTRACT

An intraoral sensor for a dental X-ray apparatus includes a detection element for detecting the X-ray radiation. The element is disposed in an interior of a housing. To improve the possibilities for cleaning and sterilizing, the housing or parts thereof are of an abrasion resistant material, in particular, of porcelain, ceramic, an enamelling, metal, or of a combination of these materials. To avoid damage to the detection element through external impacts or jarring, the element is mounted within the housing through one or more damping elements.

22 Claims, 2 Drawing Sheets

INTRAORAL X-RAY SENSOR

CROSS-REFERENCE TO RELATED APPLICATION

This is a continuing application, under 35 U.S.C. § 120, of copending international application No. PCT/EP2004/003126, filed Mar. 24, 2004, which designated the United States; this application also claims the priority, under 35 U.S.C. § 119, of German Patent Application No. 103 13 044.6, filed Mar. 24, 2003 and German Patent Application No. 103 46 287.2, filed Oct. 6, 2003; the prior applications are herewith incorporated by reference in their entirety.

BACKGROUND OF THE INVENTION

Field of the Invention

The invention lies in the field of medical devices. The present invention relates to an intraoral sensor for use with a dental X-ray apparatus. The sensor has a detection element for detection of the X-ray radiation with electronic and optical components mounted in a housing.

In dental X-ray diagnosis, in recent times, digital X-ray systems have been increasingly put to use. In comparison with classical X-ray systems, in which a radiation sensitive X-ray film is employed, which must be developed after exposure, the new digital systems offer the advantage that the X-ray image can be observed and, if appropriate, analyzed in more detail, on a screen, directly after the exposure. X-ray systems that work in accordance with these new digital methods are known, for example, from German Published, Non-Prosecuted Patent Application DE 44 02 114 A1, corresponding to U.S. Pat. No. 5,514,873 to Schulze-Ganzlin et al., German Utility Model DE 297 17 432 U1, corresponding to U.S. Pat. No. 6,169,781 to Doebert et al., or U.S. Pat. No. 5,510,623 to Sayag et al.

A conventional digital X-ray sensor is a flat, rectangular shaped housing, in the interior of which there is disposed a detection element that detects the X-ray radiation. A main component of the detection element is a semiconductor chip, for example, a Charged-Coupled Device (CCD) chip or Complementary Metal-Oxide Semiconductor (CMOS) chip, divided into a plurality of pixel regions, which detects the radiation, or the radiation converted into visible light, and, through this, produces a digital X-ray image. The signals detected by the semiconductor chip are transmitted through a cable to an evaluation unit that detects the data and presents the digital X-ray image, for example, on a screen or display.

Usually, the housing of such a digital sensor is of two plastic parts, which, after fixing of the detection element in or on one of the two housing parts, are joined together and glued with one another. Thereby, there arises the disadvantage that such a sensor cannot be sterilized because the plastic housing and, in particular, its adhesive connection cannot stand up to the high temperatures of a single or repeated sterilization. Also, with regard to the electro-optical components of the sensor, there is a risk that these components will be damaged if they are exposed to too high temperatures. On the other hand, in medicine, there is generally a need for a high standard of hygiene. Because the sensors are brought into the mouth of a patient to be investigated, there is a particular need to be able to clean and sterilize them as effectively as possible.

A further disadvantage of the known intraoral sensors lies in the mounting of the detection element within the housing. Usually, the detection element is mounted in the plastic housing either broadly on one of the base sides of the housing or at the corners. Accordingly, a problem arises because the detection elements tend to delaminate, that is, a detachment of the scintillator layer from the substrate, at their corners. The scintillator layer is necessary for the conversion of the X-ray radiation into visible light detectable by the semiconductor chip. Correspondingly, a detachment of this layer from the substrate has the consequence that, in this region, the effectiveness of the conversion of the X-ray radiation is altered, e.g., reduced or, possibly, even increased. Such an affect has the consequence that, in the region concerned, the sensor manifests an altered sensitivity, which, from a certain size of such a region, leads to the sensor overall no longer being usable.

The problem of delamination arises in particular if the sensor is jarred by impacts, for example, when it is allowed to fall. This problem is increased further in the case of the known sensors because the plastic housing is only inadequately capable of damping impacts or jarring caused from the outside.

SUMMARY OF THE INVENTION

It is accordingly an object of the invention to provide an intraoral X-ray sensor for employment in dental diagnostics that overcomes the hereinafore-mentioned disadvantages of the heretofore-known devices of this general type and that is simple to clean and, in particular, also to sterilize, and that prevents the danger of damage to the sensor, in particular, a delamination of the detection element, to the greatest possible extent.

With the foregoing and other objects in view, there is provided, in accordance with the invention, an intraoral sensor for a dental X-ray apparatus, including a housing defining an interior, at least a portion of the housing being of an abrasion resistant material, the portion including one of an entirety of the housing and a portion of the housing and an X-ray detection element for detecting X-ray radiation mounted in the interior of the housing.

With the objects of the invention in view, there is also provided an intraoral sensor for a dental X-ray apparatus, including a housing defining an interior, an X-ray detection element for detecting X-ray radiation, and at least one damping element mounting the detection element within the interior of the housing and reducing forces imparted upon the detection element.

With the objects of the invention in view, there is also provided an intraoral sensor for a dental X-ray apparatus, including a gas-tight housing defining an interior and having corners and edges, a light-sensitive semiconductor X-ray detection element for detecting X-ray radiation and transmitting data dependent upon the detected X-ray radiation, the detection element having corners, at least one damping element mounting the detection element within the interior of the housing and reducing forces imparted upon the detection element, at least one of the corners, the edges, and the damping element being of a material selected from an elastic material and a viscoelastic material, and the corners of at least one of the detection element and the housing being rounded or polygonal.

In accordance with another feature of the invention, the housing of the sensor or at least parts thereof is of an abrasion resistant material, preferably, of porcelain, ceramic, an enamelling, metal, or of a combination of these materials.

The employment of a corresponding material for the sensor housing offers the advantage that it is significantly less temperature sensitive than plastic. Accordingly, the possibility is created of sterilizing the sensor overall in the course of the previously usual sterilization procedure. The standard of hygiene that can be attained therethrough is incomparably greater than with previously known sensors.

Along with resistance to high temperatures, the indicated materials also have the advantage that they are gas-tight. In particular, the housing is gas-tight. Alongside sterilization, there correspondingly arises the possibility of treating the exterior of the sensor with ozone and, thereby, to additionally clean the sensor and, if appropriate, to carry out a disinfection.

A further aspect of the present invention is concerned with an improved mounting of the detection element within the sensor housing to avoid the danger of damage of the detection element in the case of jarring the sensor.

In accordance with a further feature of the invention, the detection element is mounted within the housing through one or more damping elements. Preferably thereby, the detection element is connected with the sensor housing through an elastic or viscoelastic element at two pair-wise oppositely lying sides. For example, the mounting may be silicone. An alternative possibility for mounting lies in a pair of sides lying opposite one another each having only in the middle a mounting point, and a second fixing is effected through mounting points disposed pair-wise perpendicular thereto, preferably, again, in the middle of the two sensor edges.

The damping mounting of the detection element has the consequence of absorbing external jarring exercised on the sensor and, therewith, significantly reducing the danger of damage. Even for the case where very rigid materials, such as, for example, porcelain, ceramic, an enamelling, or metal are employed for the sensor housing, the damping is still sufficient to ameliorate impacts and jarrings occurring upon falling down of the sensor.

On the other hand, there is, however, the possibility of further reducing the danger of damage upon falling down of the sensor if the housing is, likewise, of an elastic material, for example, of silicone. Along with an improved protection in the case of falls, through the soft configuration of the sensor housing, the acceptance by patients, who perceive a stiff element as being very uncomfortable and possibly tending towards nausea, can be significantly improved.

In accordance with an added feature of the invention, there is provided at least one damping element mounting the detection element within the housing.

In accordance with an additional feature of the invention, the at least one damping element is of a material selected from an elastic material and a viscoelastic material. In particular, the material is silicone.

In accordance with yet another feature of the invention, the housing has a flat rectangular shape with two opposing side surfaces having corresponding side walls and a given length and the at least one damping element is two damping elements connecting the detection element to the side walls over substantially the given length.

In accordance with yet a further feature of the invention, the housing has a flat rectangular shape with a first set of two opposing side surfaces and a second set of two opposing side surfaces disposed perpendicular to the first set and the at least one damping element is four damping elements, a first set of two damping elements connects the detection element to the first set of opposing side surfaces and a second set of two damping elements connects the detection element to the second set of opposing side surfaces.

In accordance with yet an added feature of the invention, the damping elements are disposed respectively in a middle of an associated one of the side surfaces.

In accordance with yet an additional feature of the invention, solely the corners and/or edges of the sensor housing are formed of an elastic or viscoelastic material, the remainder of the sensor housing being of the above-mentioned abrasion resistant materials or of plastic. Such a variant allows the advantages of an abrasion resistant housing to be combined with those of a damping or elastic covering. In the latter case, the housing of plastic and the elastic or viscoelastic material could be produced in a so-called two-component injection molding procedure. Preferably, the material is silicone.

In accordance with again another feature of the invention, the elements of the sensor, that is, the detection element and/or the housing, are configured to have the corners of the sensor correspond to the anatomy of the mouth of a patient to be investigated. Such a configuration is achieved, for example, by rounding or curving the corners or having a plurality of angled regions disposed together.

In accordance with again a further feature of the invention, the detection element has a light-sensitive, rectangular semiconductor element with at least one of rounded corners and corners with a plurality of angled regions.

In accordance with again an added feature of the invention, the detection element is a light-sensitive semiconductor element.

In accordance with again an additional feature of the invention, the light-sensitive semiconductor element is one of a CCD chip and a CMOS chip. Usually, at least the detection element—hereof in particular the CCD chip or the CMOS chip—is configured to be rectangular, which results from the process technology through the cutting of the wafer for the semiconductor chips. To adapt the form of the detection element to the anatomy of the mouth, in accordance with an advantageous exemplary embodiment, the wafer is cut in a plurality of stages, wherein the saw blade is guided in correspondence with a curved or polygonal form and, through this, a substantially rounded off corner is created. Furthermore, the wafer can be correspondingly rounded off also by milling. The rounded off or polygonal form also has the advantage that, within the scope of the anatomical conditions of the mouth, as much image information as possible can be detected for a given detection area.

In accordance with still another feature of the invention, there is provided a scintillator layer disposed before the semiconductor element.

In accordance with still a further feature of the invention, there is provided a scintillator layer disposed upstream of the semiconductor element with respect to received X-ray radiation.

In accordance with still an added feature of the invention, there is provided a light conductor layer disposed between the semiconductor element and the scintillator layer.

In accordance with a concomitant feature of the invention, there is provided a cleaning device for cleaning or disinfecting the intraoral sensor, wherein the cleaning device exposes the sensor to an ozone-containing atmosphere for a certain period of time.

Other features that are considered as characteristic for the invention are set forth in the appended claims.

Although the invention is illustrated and described herein as embodied in an intraoral X-ray sensor, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

In the figures of the drawings, unless stated otherwise, identical reference symbols denote identical parts.

Figure 1:
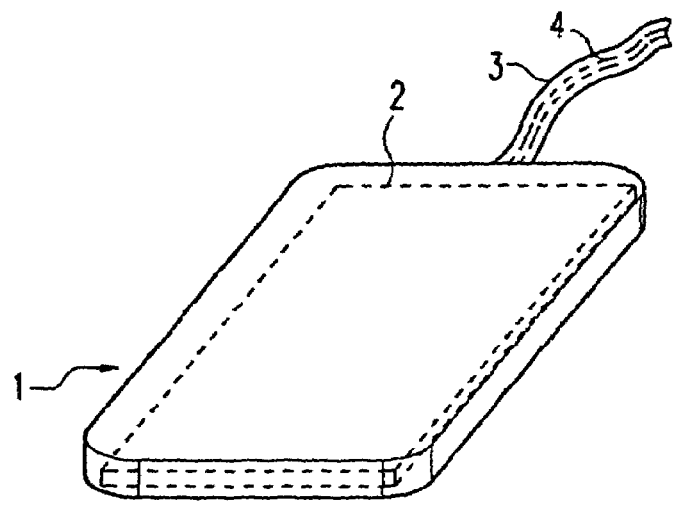
FIG. 1 is a fragmentary, partially hidden perspective view of an intraoral X-ray sensor according to the invention.
Figure 2:
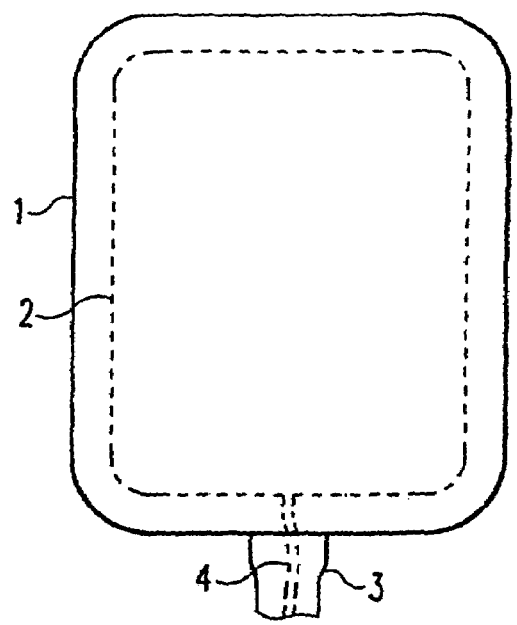
FIG. 2 is a fragmentary plan view of the sensor of FIG. 1.

Referring now to the figures of the drawings in detail and first, particularly to FIGS. 1 and 2 thereof, there is shown a flat, rectangular shaped housing 1, in the interior of which is disposed a detection element 2. At one end face of the housing 1 there is connected a cable 3 in which electric lines 4 run. The lines 4 are connected to the detection element 2. The end of the cable 3 remote from the sensor 1, 2 leads to a non-illustrated evaluation unit that receives the signals detected by the detection element 2 and produces therefrom a digital image, which is presented, for example, on a non-illustrated display of a dental treatment station.

In accordance with a first aspect of the present invention, the housing 1 is of an abrasion resistant material, for example, of porcelain, ceramic, an enamelling, or metal. Employment of these materials has the advantage to have the sensor housing 1 largely be insensitive with respect to high temperatures, thus, creating the possibility of sterilizing the sensor. In general, with the employment of the above materials or a mixture thereof, the housing 1 is significantly better to clean than plastic and, furthermore, also conveys a higher quality. Additionally, the preferred materials also have the advantage of being gas-tight. Thus, cleaning the sensor with ozone is made possible, which cleaning, otherwise, would attack the electronic components in the interior of the housing 1. Such a cleaning device 20 is shown diagrammatically in FIG. 3.

A particular feature of the housing 1 illustrated in FIGS. 1 and 2 and the detection element 2 disposed within the housing 1, lies in providing both elements with rounded off corners. Through this, the form of the sensor is adapted to the anatomy of the mouth. Correspondingly, the introduction and placing of the sensor within the mouth during the X-ray investigation is made more pleasant for the patient.

The rounded off configuration of the sensor housing 1 can be effected without further difficulty. In contrast, it is more problematic to round off also the detection element 2, in particular, the CCD chip or CMOS chip disposed thereon. The shaping of the chip is effected, as a rule, through the sawing of a wafer, for which reason usually rectangular chips, having 90° angle corners, are put to use. To also configure the detection element 2 with rounded-off corners, or with at least practically rounded off corners, in the present case, the wafer is cut in a number of stages where the saw blade is guided in correspondence with the desired curved shape. Alternatively, the initially entirely rectangular cut chip could be milled into the rounded off form. Thereby, although the rounded off form of the detection element 2, taken for itself, does not have effect on the well-being of the patient, this shape is, however, desirable because, with the employment of a rounded off housing 1, the available region can be optimally exploited and, thus, detection of a maximum of image information can be made.

The employment of the above-mentioned preferred materials, porcelain, ceramic, an enamelling, or metal has the consequence that the sensor housing 1 is still stiffer than in the case of the previously preferred employment of plastic. Through the stiff material, impacts or jarrings caused from the outside would be transferred to the detection element mounted in the interior of the housing 1 particularly effectively. Thus, an increased risk of damage to the detection element 2 is present. Accordingly, with reference to FIGS. 3 and 4, there are described possibilities of better protecting the detection element 2 against such external impacts and jarrings.

Figure 3:
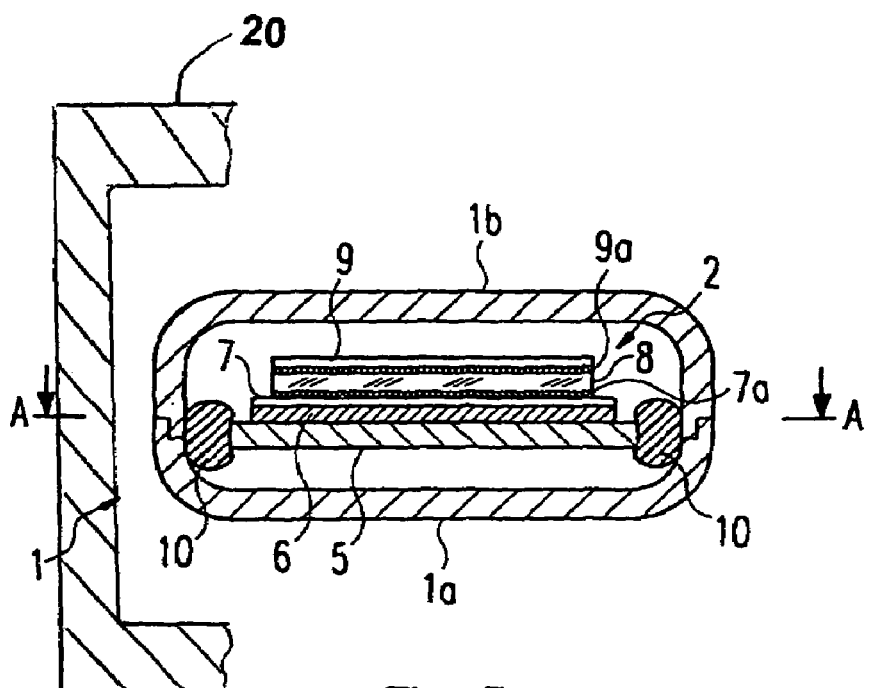
FIG. 3 is a cross-sectional view of the sensor of FIGS. 1 and 2.

FIG. 3 shows the sensor according to the present invention in cross-section. The detection element 2 is of a substrate 5, serving as a carrier element, on the upper side of which is applied an X-ray radiation screening layer 6. However this screening layer 6 could be omitted. On the upper side of the screening layer 6, or on the upper side of the substrate 5, there is located the light sensitive element 7, that is, a CCD chip or a CMOS chip for spatially resolved detection of image information.

Because the CCD chip or the CMOS chip is significantly more sensitive for visible light than for the X-ray radiation, the sensitivity of the detection element 2 is increased by disposing, before the semiconductor layer 7, a light conductor layer 8 and a scintillator layer 9.

The scintillator layer 9 serves to convert incident X-ray radiation, through scintillation effects, into visible light, which is transferred through the light conductor layer 8 to the semiconductor layer 7. The light conductor layer 8 is, thereby, configured so that the X-ray radiation incident on a particular location of the scintillator layer 9 is also detected as visible light in substance at the corresponding location of the semiconductor layer 7 lying therebelow. Through such a configuration, the detection sensitivity of the detection element 2 is significantly increased, the resolving power being only insignificantly affected.

The structure illustrated in FIG. 3 corresponds in substance to the classical structure of a detection element for an intraoral digital sensor, whereby—as already mentioned—it is possible for the screening layer 6 and/or the light conductor layer 8 to be omitted. Usually, the detection element is attached in the sensor housing mounted at the corners or over an area at one of the two base sides of the housing lower part 1a or of the housing upper part 1b. With these conventionally employed mountings, however, external impacts or jarrings exercised on the housing are transferred virtually unreduced to the detection element. In such a configuration, a risk of damage to the detection element is present, in particular, there is risk of scintillator layer 9 detachment.

In such a context, the semiconductor layer 7 with the light conductor layer 8 or the light conductor layer 8 with the scintillator layer 9 are held together through adhesion or coupling layers 7a and 9a in each case therebetween. For a case where the light conductor layer 8 is omitted, the scintillator layer 9 is usually produced on its own (non-illustrated) substrate, whereby the composite including the scintillator layer 9 and the associated substrate is, again, glued by the adhesion layer 7a to the semiconductor layer 7. If such a configuration is now exposed to jarring or strong impacts, there is a risk that the coupling effect of the adhesion or coupling layers 7a, 9a reduces and that the various layers of the composite detach from one another. If this occurs, sensitivity of the sensor may be partially altered, which could make the sensor unusable.

It is to be remarked further that, instead of employing adhesion layers there is also the possibility of pressing the scintillator layer 9 onto the light conductor layer 8 or the semiconductor layer 7. However, also in the case of this variant, there is a risk that the scintillator layer 9, due to jarring, detaches from its base and, thus, damage occurs to the sensor.

To prevent damage, also in the case of the above-mentioned particularly rigid materials for the housing 1, to the detection element 2, the element 2 is mounted within the housing 1 by way of a particular damping. The mounting is achieved by two or more damping elements 10, through which the side edges of the detection element 2 are connected with the corresponding inner walls of the sensor housing 1. The damping elements 10 are of an elastic or viscoelastic material with inherent damping, for example, they are of silicone.

Figure 4A:
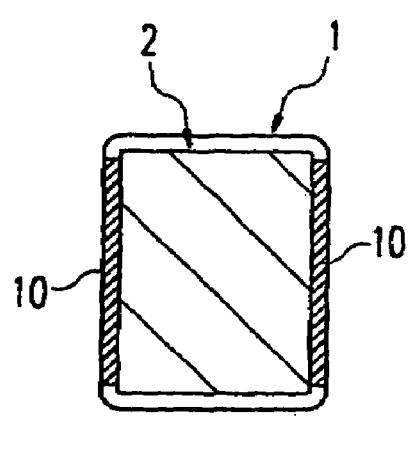
FIG. 4A is a cross-sectional view of the sensor of FIG. 3 along section line A—A illustrating a first exemplary possibility for mounting the detection element within the housing.

In the case of a first possible mounting variant, which is schematically illustrated in FIG. 4A, two sides of the detection element 2, lying opposite to one another, are connected with the housing 1 over their entire respective lengths through two relatively long damping elements 10.

Figure 4B:
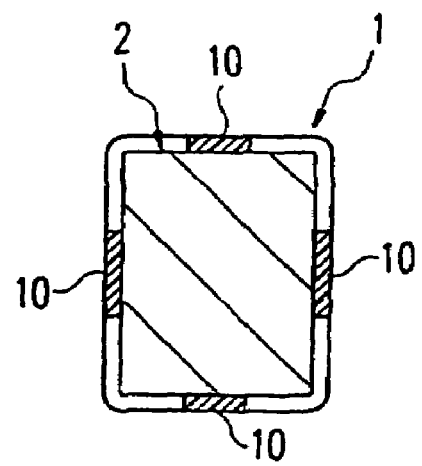
FIG. 4B is a cross-sectional view of the sensor of FIG. 3 along section line A—A illustrating a second exemplary possibility for mounting the detection element within the housing.

As an alternative mounting, illustrated in FIG. 4B, two sides lying opposite to one another are connected with the sensor housing 1 respectively only in their middle region through two relatively shorter damping elements 10 and, at the other sides perpendicular thereto, two damping elements 10 are likewise disposed. These elements 10 are, again, preferably respectively disposed in the middle of the edges of the detection element 2.

The damping mounting of the detection element 2 within the sensor housing 1, in accordance with the present invention, has the consequence of absorbing external jarrings exercised on the housing and, thus, suppressing the danger of damage of the detection element 2 to the greatest possible extent. This reduction is particularly significant if the sensor housing 1 is of a material that, itself, is not damping, for example, if it is of porcelain, ceramic, or metal. The employment of the above-mentioned materials and the damping mounting in accordance with the present invention, thus, makes it possible to realize an intraoral sensor that, on one hand, can be cleaned particularly well and effectively, and, on the other hand, avoids the risk of damage of the detection element through external impacts or jarrings.

If, rather, it is primarily desired to avoid damage to the detection element upon falling down of the sensor, also the housing or its corners and/or edges can be of a soft or damping material, for example, of silicone. The employment of a corresponding material also for the sensor housing also would have the advantage of being significantly more pleasant for patients, in particular, for older patients or children and, thus, the acceptance of digital X-ray techniques in dental diagnosis can be increased.

I claim:

1. An intraoral sensor for a dental X-ray apparatus, comprising:
    a housing defining an interior with inner walls;
    an X-ray detection element for detecting X-ray radiation, said X-ray detection element having side edges; and
    at least two damping elements mounting said detection element within said interior of said housing and reducing forces imparted upon said detection element, said at least two damping elements connecting said side edges of said X-ray detection element to said inner walls of said housing.

2. The intraoral sensor according to claim 1, wherein at least a part of said housing is of a material selected from the group consisting of porcelain, ceramic, an enamelling, metal, and a combination of porcelain, ceramic, an enamelling, and metal.

3. The intraoral sensor according to claim 1, wherein:
    said housing has corners and edges; and
    at least one of said corners and said edges are of a material selected from an elastic material and a viscoelastic material.

4. The intraoral sensor according to claim 3, wherein said material is silicone.

5. The intraoral sensor according to claim 1, wherein said at least two damping elements are of a material selected from an elastic material and a viscoelastic material.

6. The intraoral sensor according to claim 5, wherein said material is silicone.

7. The intraoral sensor according to claim 1, wherein:
    said housing has a flat rectangular shape with two opposing side surfaces having corresponding side walls and a given length; and
    said at least two damping elements connect said detection element to said side walls over substantially said given length.

8. The intraoral sensor according to claim 1, wherein:
    said housing has a flat rectangular shape with a first set of two opposing side surfaces and a second set of two opposing side surfaces disposed perpendicular to said first set; and
    said at least two damping elements are four damping elements, a first set of two damping elements connects said detection element to said first set of opposing side surfaces and a second set of two damping elements connects said detection element to said second set of opposing side surfaces.

9. The intraoral sensor according to claim 8, wherein said damping elements are disposed respectively in approximately a middle of an associated one of said side surfaces.

10. The intraoral sensor according to claim 1, wherein at least one of said detection element and said housing are shaped to correspond to an anatomy of a mouth.

11. The intraoral sensor according to claim 10, wherein:
    at least one of said detection element and said housing have corners; and
    said corners are one of rounded and polygonal.

12. The intraoral sensor according to claim 10, wherein said detection element has a light-sensitive, rectangular semiconductor element with at least one of rounded corners and corners with a plurality of angled regions.

13. The intraoral sensor according to claim 1, wherein said detection element has a light sensitive rectangular semiconductor element with at least one of rounded corners and corners with a plurality of angled regions.

14. The intraoral sensor according to claim 1, wherein said detection element is a light-sensitive semiconductor element.

15. The intraoral sensor according to claim 14, wherein said light-sensitive semiconductor element is one of a CCD chip and a CMOS chip.

16. The intraoral sensor according to claim 14, further comprising a scintillator layer disposed before said semiconductor element.

17. The intraoral sensor according to claim 14, further comprising a scintillator layer disposed upstream of said semiconductor element with respect to received X-ray radiation.

18. The intraoral sensor according to claim 17, further comprising a light conductor layer disposed between said semiconductor element and said scintillator layer.

19. The intraoral sensor according to claim 1, wherein said housing is gas-tight.

20. The intraoral sensor according to claim 1, further comprising an ozone-cleaning device for exposing at least one of said housing and said detection element to an ozone-containing atmosphere for a period of time.

21. An intraoral sensor for a dental X-ray apparatus, comprising:
   a housing defining an interior with inner walls, at least a part of said housing being of an abrasion resistant material, said part including one of an entirety of said housing and a portion of said housing;
   an X-ray detection element for detecting X-ray radiation mounted in said interior of said housing, said X-ray detection element having side edges; and
   at least two damping elements mounting said detection element within said interior of said housing and reducing forces imparted upon said detection element, said at least two damping elements connecting said side edges of said X-ray detection element to said inner walls of said housing.

22. An intraoral sensor for a dental X-ray apparatus, comprising:
   a gas-tight housing defining an interior with inner walls and having corners and edges;
   a light-sensitive semiconductor X-ray detection element for detecting X-ray radiation and transmitting data dependent upon said detected X-ray radiation, said detection element having corners and side edges;
   at least two damping elements mounting said detection element within said interior of said housing and reducing forces imparted upon said detection element, said at least two damping elements connecting said side edges of said X-ray detection element to said inner walls of said housing;
   at least one of said corners, said edges, and said damping elements being of a material selected from an elastic material and a viscoelastic material; and
   said corners of at least one of said detection element and said housing being rounded or polygonal.

* * * * *